United States Patent [19]

Le Roy

[11] 4,073,298
[45] Feb. 14, 1978

[54] WOUND CLIP
[75] Inventor: Pierre L. Le Roy, Wilmington, Del.
[73] Assignee: New Research & Development Lab., Inc., Wilmington, Del.
[21] Appl. No.: 711,250
[22] Filed: Aug. 3, 1976
[51] Int. Cl.² .................................................. A61B 17/08
[52] U.S. Cl. ................................... 128/337; 24/206 R
[58] Field of Search ............... 128/334 R, 334 C, 335, 128/336, 337, 346; 24/87 R, 206 R

[56] References Cited
U.S. PATENT DOCUMENTS

| 268,632 | 12/1882 | Danforth | 128/337 |
| 380,093 | 3/1888 | Cruice et al. | 128/336 |
| 1,373,507 | 4/1921 | Hyde | 24/87 R |
| 2,461,605 | 2/1949 | Huntsman | 24/206 R |
| 2,471,694 | 5/1949 | Maestri | 24/206 R |
| 3,385,299 | 5/1968 | Le Roy | 128/337 |
| 3,825,010 | 7/1974 | McDonald | 128/337 |
| 3,971,384 | 7/1976 | Hasson | 128/335 |

Primary Examiner—Dalton L. Truluck
Attorney, Agent, or Firm—Connolly and Hutz

[57] ABSTRACT

A wound clip includes a base member having a thickened head portion from which tines extend and a lateral bridging member which slides in a housing. The housing also has tines and incorporates a locking member which is selectively locked in place by being inserted in a selective one of a plurality of aligned detents in the bridging member.

12 Claims, 3 Drawing Figures

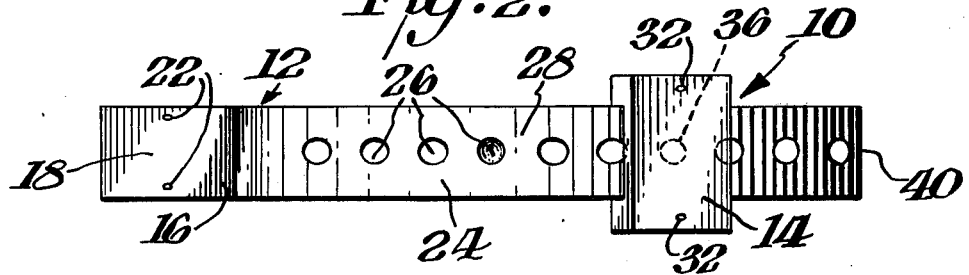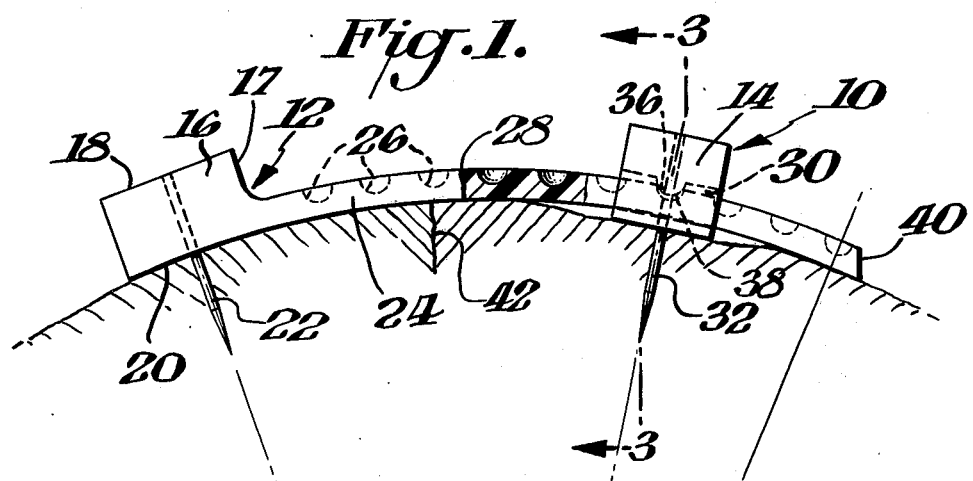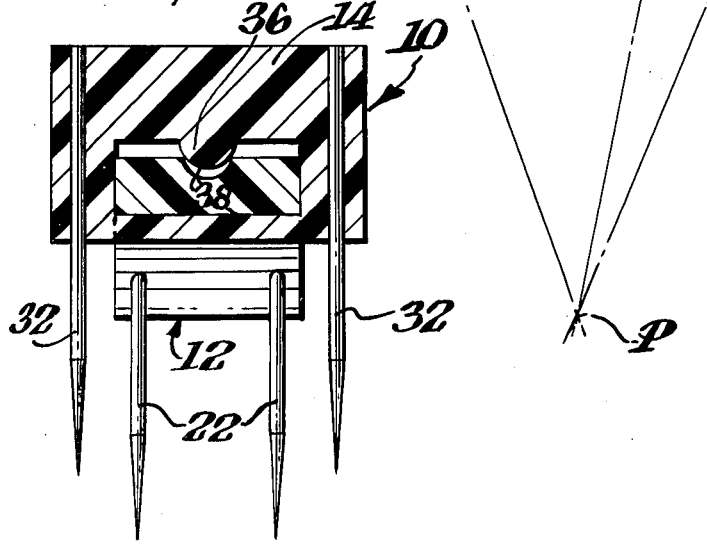

WOUND CLIP

BACKGROUND OF THE INVENTION

U.S. Pat. No. 3,385,299 discloses a wound clip which is particularly effective in closing wound flaps as a quick and convenient replacement for conventional suturing techniques. The wound clip of that patent incorporates ratchet teeth along the sides of a member which slides in a housing. The ratchet teeth are selectively engaged by a spring fitting in slots in the housing. While this arrangement is effective it does require a certain amount of force to disengage the spring for permitting release of the ratchet whereby the sliding action may take place. It would be desirable to avoid the necessity of such manipulations by providing simpler methods of manipulations by the nurse or technician without any hampering in the degree of effectiveness. It would also be desirable to minimize the number of separate components by, for example, avoiding the necessity of using a completely detachable spring as in the above patent.

A further prior ratchet type arrangement is the suture clamp of U.S. Pat. No. 268,632.

The present invention is particularly directed to human application. There exists in other arts various other devices. For example, U.S. Pat. No. 380,093 relates to a hoof clasp which includes a pair of relatively slidable members each of which terminates in a series of hooks or prongs for securement into the hoof. One of the members terminates in an undulated or grooved portion which is intended to cooperate with a bent tongue in the other member. The locking action generally takes place above the crack rather than at a more secured area such as the area where the device itself is anchored. Additionally, the clasp is made of a sheet metal material which would tend to be deformed thus limiting its useful life.

SUMMARY OF THE INVENTION

An object of this invention is to provide a wound clip using a minimal number of parts.

A further object of this invention is to provide such a wound clip which may be conveniently and effectively used in a simple manner.

A still further object of this invention is to provide such a wound clip which may be economically and conveniently made of readily available and relatively inexpensive plastic materials while maximizing their effectiveness.

In accordance with this invention a wound clip includes a base member having a thickened head portion from which tines extend and a lateral bridging member which slides in a housing. The housing also has tines and incorporates a locking member which is selectively locked in place by being inserted in a selective detent in the bridging member.

The locking member is preferably a cylindrical lug which extends into the slot of the housing in line with the tines. The detents are preferably a series of aligned holes in the bridging member. The resilient nature of the material itself is preferably utilized to permit the lug to enter and be withdrawn from the detents.

Stability is enhanced by providing the tines in a thickened portion of the base member and similarly by providing the opposite tines in the housing which itself is thickened as compared to the relatively thin bridging member.

THE DRAWINGS

FIG. 1 is a side elevation view partly in section of a wound clip in accordance with the invention;

FIG. 2 is a top plan view of the wound clip of FIG. 1; and

FIG. 3 is a cross-sectional view taken through FIG. 1 along the line 3—3 and showing the structure of the wound clip as detached from the patient.

DETAILED DESCRIPTION

As indicated in the drawings, the wound clip 10 includes an elongated base member 12 and a housing 14. Base member 12 has a thickened head portion 16 at one end thereof with an upper surface 18 and a lower surface 20. A pair of tines are mounted in and extend completely through head portion 16 extending outwardly from lower surface 20. The tines 22 terminate in points for convenient anchoring into the patient. Secured laterally of and integral with head portion 16 is a thin flat bridging member 24 which is provided with a plurality of longitudinally aligned detents 26 in its upper surface 28 thereof. Detents 26 may be dished-out depressions or may be holes extending completely through the bridging member.

Housing 14 is likewise of thickened dimension being slightly thicker than head portion 16. Slot 30 extends longitudinally completely through housing 14 and is of sufficient dimension whereby bridging member 24 may slide therein. A tine 32 is disposed on each side of slot 30 and extends completely through housing 14. Tines 32 are similar to but slightly longer than tines 22. A vertical bore may be formed in housing 14 midway between and generally aligned with tines 32. Into the bore is pressed fit or otherwise secured a cylindrical lug 36 which is disposed for being selectively positioned in the various detents 26. Alternatively as best shown in FIG. 3, lug 36 may be molded integrally with housing 14 without any special bore. A suitable material such as the readily available plastics is selected for clip 10 which has sufficient resiliency that bridging member 24 may be telescoped through slot 30 with lug 36 moving into and being forced out of the detents 26. Lug 36 terminates in a rounded face 38 (FIG. 3) to act as a camming surface to facilitate the riding action of the lug into and out of detents 26.

In operation tapered end 40 of bridging member 24 is inserted in slot 30 of housing 14. The taper facilitates the positioning of the bridging member 24 in the slot 30. The parts are manipulated until bridging member 24 has been telescoped a sufficient amount. As is apparent from FIG. 1, the components and particularly base member 12 are arcuate for generally conforming to the curvature of the head of the patient where the clip is particularly intended to be used for closing cranial wound flaps. This telescoping step is preferably accomplished at a convenient time prior to the closing of the wound flap so that a series of such clips 10 is ready for application on the patient. Each clip 10 is then positioned above the incision 42 so that the pairs of tines 22, 32 are generally equally spaced on each side of incision 42. Clip 10 is then pushed downwardly to anchor the tines into the skull and thus serve as a suture. It has been found that a series of such clips 10 may be quickly and conveniently applied with minimal effort to completely close a wound flap.

As is apparent from FIG. 1, tines 22 and tines 32 are inclined toward each other along imaginary lines 34, 35 which intersect at an imaginary point P. Lug 36 is likewise inclined along the same imaginary line 35 as its corresponding tines 32 and is so arranged with respect to detents 26, that the imaginary point P of intersection remains constant regardless of which detent 26 of lug 36 is associated with. Imaginary line 35', for example, corresponds to the orientation of tines 32 if the last detent 26 had been engaged by lug 36.

By disposing lug 36 midway between tines 32 along the longitudinal centerline of housing 14 and by locating detents 26 along the longitudinal centerline of bridging member 24, housing 14 is reversible. Thus in assemblying the parts it makes no difference into which end of slot 30 tapered end 40 is inserted since lug 36 will still be in proper position for engaging detents 26.

As is apparent from FIG. 1 head portion 16 has a leading face 17 at its junction with bridging member 24 between tines 22 and housing 14. Leading face 17 extends upwardly above the upper surface 28 of bridging member 24 and thus, as apparent from the drawings, is dimensioned so as to be prevented from being telescopically received in slot 30 and accordingly necessarily limits the extent of telescopic action.

As previously indicated clip 10 may be made of any suitable material. For example, a plastic such as Lexan is particularly effective since it is stiff and rigid yet inherently has sufficient resiliency to permit lug 36 to move into and out of detents 36. Although lug 36 is shown being integral with housing 14, as previously indicated the lug may be a separate member inserted in a bore in the housing. The invention may also be practiced in various other manners wherein other means may also be utilized such as mounting lug 36 for its up and down movement by means of a spring positioned in the bore located adjacent the top surface of housing 14. With such separate spring means it would not be necessary to utilize a resilient material since the necessary resiliency for the locking and unlocking action would be accomplished by means of the spring.

What is claimed is:

1. A wound clip for use on wound flaps in surgical use comprising an elongated base member, said base member having a head portion at one end of said base member, said head portion having an upper surface and a lower surface, first tine means mounted in said head portion extending outwardly from said lower surface, said first tine means terminating in points disposed remote from said lower surface, said base member having a thin flat bridging member permanently secured to said head portion laterally thereof, said head portion being substantially thicker than said bridging member, said bridging member having an upper surface and a lower surface, a plurality of longitudinally aligned detents in said upper surface of said bridging member, a housing, said housing being substantially thicker than said bridging member, said housing having a horizontal slot extending laterally completely therethrough, said slot being dimensioned for telescopically receiving said bridging member whereby said bridging member may slide in said housing while being maintained in the same lateral orientation in said housing as it does outside said housing, said head portion having a leading face at its junction with said bridging, said leading face being dimensioned to be prevented from being telescopically received in said slot, said leading face being disposed between said first tine means and said housing, second tine means comprising a pair of tines extending from the lower surface of said housing and terminating in points thereof, a locking member mounted in said housing and projecting downwardly into said slot in the generally central area thereof, said locking member being positioned for selectively entering said detents as said bridging member slides in said slot for locking said housing and said base member together whereby said first and said second tine means may be anchored into the patient on opposite sides of a wound flap incision with said bridging member spanning the incision, said clip including resilient means to permit said locking member to selectively move into and out of said detents, and said locking member being a lug permanently fixed to said housing and located in said housing in the general area of said second tine means in line with and between said tines to confine the locking action in the vicinity of said thickened housing where said housing is anchored.

2. The clip of claim 1 wherein said bridging member is made of a resilient material to comprise said resilient means.

3. The clip of claim 2 wherein said locking member is a cylindrical lug secured in an aperture in said housing, said lug terminating in a rounded face.

4. The clip of claim 3 wherein said detents are of circular shape when viewed from said upper surface of bridging member.

5. The clip of claim 3 wherein said detents are holes extending completely through said bridging member.

6. The clip of claim 1 wherein said bridging member is made of a resilient material to comprise said resilient means.

7. The clip of claim 1 wherein said locking member is a cylindrical lug secured in an aperture in said housing, said lug terminating in a rounded face.

8. The clip of claim 7 wherein said detents are of circular shape when viewed from said upper surface of bridging member.

9. The clip of claim 1 wherein said first tine means includes a pair of tines aligned with each other, said pair of tines of said second tine means being aligned with each other, said first and said second tine means being inclined toward each other along imaginary lines which intersect at an imaginary point, and said locking member being inclined at the same angle as said second tine means and being arranged with respect to said detents for maintaining said imaginary point constant regardless of which of said detents is engaged by said locking member.

10. The clip of claim 1 wherein said tines of said first tine means extend completely through said head portion, said tines of said second tine means extending completely through said housing, and the end of said bridging member remote from said head portion being tapered to facilitate the insertion of said bridging member into said slot.

11. The clip of claim 1 wherein said locking member is a cylindrical lug, said lug being disposed along the longitudinal centerline of said housing, and said detents being located along the longitudinal centerline of said bridging member whereby said locking member may function regardless of which end of said housing said bridging member is inserted into.

12. The clip of claim 1 wherein said detents are spaced apart uniformly, said housing being of a length about equal to the distance between three detents to minimize the length of said housing for receiving only a single full detent therein in which said lug is engaged, and said bridging member being integral with said head portion.

* * * * *